United States Patent
Kawanishi et al.

(10) Patent No.: US 6,806,269 B1
(45) Date of Patent: Oct. 19, 2004

(54) 2-AMINO-BENZOXAZINONES FOR THE TREATMENT OF HERPES SIMPLEX VIRUS

(75) Inventors: Masashi Kawanishi, Shizuoka-ken (JP); Wataru Takahashi, Shizuoka-ken (JP)

(73) Assignee: G. D. Searle & Cop, Chicago, IL (US)

( * ) Notice: Subject to any disclaimer, the term of this patent is extended or adjusted under 35 U.S.C. 154(b) by 132 days.

(21) Appl. No.: 10/030,414

(22) PCT Filed: Jul. 11, 2000

(86) PCT No.: PCT/US00/18817

§ 371 (c)(1),
(2), (4) Date: May 24, 2002

(87) PCT Pub. No.: WO01/03697

PCT Pub. Date: Jan. 18, 2001

Related U.S. Application Data

(60) Provisional application No. 60/142,956, filed on Jul. 12, 1999.

(51) Int. Cl.[7] .................... C07D 265/22; A61K 31/536

(52) U.S. Cl. ....................................... 514/230.5; 544/92
(58) Field of Search ................. 514/230.5, 92

(56) References Cited

U.S. PATENT DOCUMENTS 5,985,872 A   11/1999   Abood et al.

FOREIGN PATENT DOCUMENTS

WO   WO 96/37485   11/1996

OTHER PUBLICATIONS

Bioorganic & Medicinal Chemistry Letters, vol. 7, No. 16, pp. 2105–2108, 1997.
Tetrahedron 54 (1998) pp. 4013–4031.

*Primary Examiner*—Richard L. Raymond
(74) *Attorney, Agent, or Firm*—Banner & Witcoff Ltd.

(57) ABSTRACT

2-Amino-benzoxazinones are identified for use in the treatment of Herpes Simplex Virus. A subject is treated for Herpes Simplex Virus by treating with an effective amount of 2-amino-benzoxazinones

3 Claims, No Drawings

2-AMINO-BENZOXAZINONES FOR THE TREATMENT OF HERPES SIMPLEX VIRUS

This is a U.S. National Phase Application Under 35 USC 371 and applicants herewith claim the benefit of priority of PCT/US00/18817 filed Jul. 11, 2000, which was published Under PCT Article 21(2) in English and Application No. 60/142,956 filed in the United States of America on Jul. 12, 1999.

FIELD OF THE INVENTION

This invention is in the field of antiviral agents and specifically relates to compounds, compositions and methods for treating Herpes Simplex Virus.

BACKGROUND OF THE INVENTION

There is a great need for new therapies for the treatment of viral diseases. Whereas there has been great progress in developing a variety of therapies for the treatment of bacterial infections, there are few viable therapies for the treatment of viruses. Zidovudine is the primary approved treatment for human immunodeficiency virus. Ganciclovir, acyclovir, and foscarnet are currently utilized for the treatment of herpesvirus infections. However, these therapies can have substantial side effects based on their deleterious effects on host cell DNA replication or their effect on a limited number of viral infections. In addition, viruses are known to develop resistance to therapies, which causes a progressive decline in efficacy.

Viruses are classified into broad categories based on whether they incorporate RNA or DNA. Important virus families classified of the DNA type include adenoviridae, poxviridae, papovaviridae and herpesviridae.

Herpesviridae is a family of DNA viruses which include herpes simplex virus type-1 (HSV-1), herpes simplex virus type-2 (HSV-2), cytomegalovirus (CMV), varicella-zoster virus (VZV), Epstein-Barr virus, human herpesvirus-6 (HHV6), human herpesvirus-7 (HHV7), human herpesvirus-8 (HHV8), pseudorabies and rhinotracheitis, among others.

It is known that herpesviruses express their genetic content by directing the synthesis of a number of proteins encoded by the herpesvirus DNA in the host cell. One of the important virus-encoded proteins is made as a precursor consisting of an amino terminal-located protease and carboxyl terminal-located assembly protein. This precursor is proteolytically processed in an autocatalytic manner at a specific amino acid sequence known as the "release" site yielding separate protease and assembly protein. The assembly protein is cleaved further by the protease at another specific amino acid sequence known as the "maturation" cleavage site. Recently, EP 514,830, published Nov. 25, 1992, describes a virus-specific serene protease which has a role in herpesvirus replication. Additionally, Lui and Roizman (*J. Virol*, 65, 5149 (1991)) describe the sequence and activity of a protease and the associated assembly protein encoded by $U_L26$ of HSV-1. A. R. Welch et al. (*Proc. Natl. Acad. Sci. USA*, 88, 10792 (1991) and WO93/01291, published Jan. 21, 1993) describe the related protease (also known as assemblin) and assembly protein encoded by $U_L80$ of CMV. An approach currently being investigated for potential use in the treatment of herpesvirus infections is the development of inhibitors of herpesvirus proteases.

4H-3,1-Benzoxazinones have been described in the literature as having serine protease activity, among others. For example, Teshima et al. (*J. Biol. Chem.*, 257, 5085–5091 (1982)) describes various 2-alkyl-4H-3,1-benzoxazin-4-ones as enzyme inhibitors. Moorman and Abeles (*J. Amer. Chem. Soc.*, 104, 6785–6786 (1982)) describes 4H-3,1-benzoxazin-2,4-dione as having some enzyme inhibitory activity. R. Stein, et al. (*Biochemistry*, 26, 4126–4130, (1987)) describes 2-alkyl-4H-benzoxazin-4-ones, with further substitution at the 5, 6 and 7 positions, as inhibiting the elastase enzyme. WO92/18488 (published Oct. 29, 1992) describes 2-alkyl-4H-3,1-benzoxazin-4-ones with substitution at the 5 and 7 positions as selective inhibitors of elastase. EP Pub. 206,323 (published Dec. 30, 1985) describes 2-alkoxy-, 2-aryloxy- and 2-aralkoxy-4H-3,1-benzoxazin-4-ones, having substitution at the 5, 6, 7 and 8 positions, as enzyme inhibitors. U.S. Pat. No. 4,745,116 to A. Kranz et al. describes 2-alkoxy, 2-aryloxy- and 2-aralkoxy-4H-3,1-benzoxazin-4-ones, having further substitution at the 5, 7 and 8 positions, as enzyme inhibitors. U.S. Pat. No. 5,428,021 to Hiebert et al. describes 6-(aminoacid)amino-2-alkoxybenzoxazinones as elastase inhibitors. WO 96/07648, published Mar. 14, 1996, describes 2-phenylamino-benzoxaziones for the treatment of Alzheimer's, and specifically 6-chloro-2-(2-iodophenylamino)-benzo[d][1,3]oxazin-4-one is described.

2-Amino-4H-3,1-benzoxazinones have been described. A Krantz et al. (*J. Med. Chem.*, 33, 464–479 (1990)) describes 4H-3,1-benzoxazin-4-ones substituted with alkyl, alkylamino, alkoxy and alkylthio substituents at the 2-position, and with further substitution at the 5, 6 and 7 positions, as elastase inhibitors. Uejima et al. (*J. Pharm. Exp. Ther.*, 265, 516–522 (1993)) describe 2-alkylamino-5-methyl-7-acylamino-4H-3,1-benzoxazin-4-ones as highly selective elastase inhibitors with significant plasma stability. U.S. Pat. No. 4,657,893 to Krantz et al. describes 2-alkylamino- and 2-alkylurido-4H-3,1-benzoxazin-4-ones having further substitution at the 5,7 and 8 positions, as enzyme inhibitors.

F. L. M. Alvarez (*An. Quim.*, 79, 115–17 (1983)) describes the preparation of 2-sulfonylamino-4H-3,1-benzoxazinones. J. G. Tercero et al. (*An. Quim.*, 83, 247–50, (1987)) describes the preparation of 2-arylsulfonylamino-4H-3,1-benzoxazinones.

I. Butula et al. (*Croat. Chem. Acta*, 54, 105–8 (1981)) describe the synthesis of 2-alkylamino-4H-3,1-benzoxazinones. H. Urich et al. (*J. Org. Chem.*, 32, 4052–53 (1967)) describes the synthesis of 2-alkylamino-4H-3,1-benzoxazinones. E. Papadopoulos (*J. Heterocyclic. Chem.*, 21, 1411–14 (1984)) describes the use of 2-haloalkylamino-4H-3,1-benzoxazin-4-one as a starting material for the synthesis of phenylureas. EP Appln. 466,944 (published Jan. 22, 1992) describes 2-alkylamino-7-acylamino-5-alkyl-4H-benzoxazin-4-ones as selective enzyme inhibitors of elastase.

M. Badawy et al. (*J. Heterocyclic. Chem.*, 21, 1403–4 (1984)) describe the use of N-phenyl-2-amino-4H-3,1-benzoxazin-4-one as a starting material for the synthesis of quinazolines. R Khan et al. (*J Chem. Research*(S), 342–43 (1992) describe the synthesis of 2-[5-aryl-1,3,4-oxadiazol-2-yl]amino-4H-3,1-benzoxazin-4-ones.

WO 96/37485 describes antiviral agents and compounds, compositions, and methods for treating herpes-related disorders. This document does not describe compounds that have specificity to HSV.

SUMMARY OF THE INVENTION

It was discovered that specific compounds that fall within the generic scope of Formula II of WO 96/37485 are very effective against HSV at lower concentrations than the compounds of the examples specifically disclosed in WO 96/37485. The compounds of the present invention have specificity to HSV. This specificity is deemed to be derived from structural conformation of the compounds having $R^{28}$ and $R^{29}$ substituents.

The present invention is directed to a compound of Formula II:

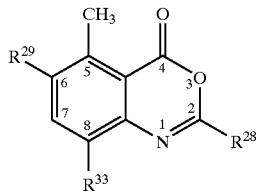

II wherein $R^{28}$ is selected from amino optionally substituted with two radicals selected from alkyl, aralkyl, heterocyclylalkyl, heterocyclyl, and aryl;

wherein $R^{29}$ is selected from

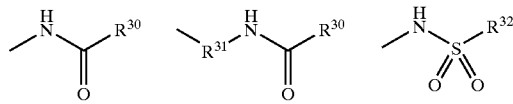

wherein $R^{30}$ is selected form alkyl, alkoxy, alkylamino, carboxyalkyl, alkoxylky, alkylaminoalkyl, cycloalkyl, heterocyclyl, heterocyclylalkyl,aralkyl, aralkoxy, aryloxy, cycloalkyloxy, arylamino, aralkenyl, heterocyclylalkoxy, alkylaminoalkoxy, alkylaminoalkylamino, heterocyclylalkylamino, N-aryl-N-alkylamino, and N-aralkylamino; wherein $R^{31}$ is alkyl; wherein $R^{32}$ is selected from alkyl and aryl; and wherein $R^{33}$ is selected from hydrido, halo and alkyl;

or a pharmaceutically-acceptable salt thereof.

The present invention is further directed to a pharmaceutical composition comprising a therapeutically-effective amount of a compound of formula II and a pharmaceutically acceptable carrier or diluent.

The present invention is further directed to a method or therapeutic or prophylactic treatment of Herpes Simplex Virus in a subject, said method comprising treating said subject with an effective amount of a compound of formula II.

DETAILED DESCRIPTION OF THE INVENTION

The present invention relates to a class of substituted benzoxazinones, useful in the therapeutic and prophylactic treatment of Herpes Simplex Virus viral infections, as defined by Formula II:

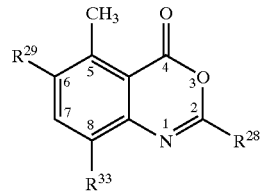

II wherein $R^{28}$ is selected from amino optionally substituted with two radicals selected from alkyl, aralkyl, heterocyclylalkyl, heterocyclyl, and aryl, or the nitrogen can form a member of a heterocyclic ring;

wherein $R^{29}$ is selected from

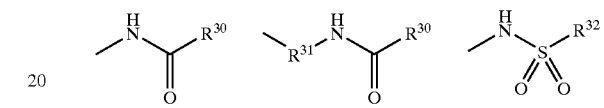

wherein $R^{30}$ is selected form alkyl, alkoxy, alkylamino, carboxyalkyl, alkoxyalkyl, alkylaminoalkyl, cycloalkyl, heterocyclyl, heterocyclylalkyl, aralkyl, aralkoxy, aryloxy, cycloalkyloxy, arylamino, aralkenyl, heterocyclylalkoxy, alkylaminoalkoxy, alkylaminoalkylamino, heterocyclylalkylamino, N-aryl-N-alkylamino, and N-aralkylamino; wherein $R^{31}$ is alkyl; wherein $R^{32}$ is selected from alkyl and aryl; and wherein $R^{33}$ is selected from hydrido, halo and alkyl;

or a pharmaceutically-acceptable salt thereof

An even more preferred class of compounds consists of those compounds of Formula II wherein $R^{28}$ is selected from amino optionally substituted with two radicals selected from lower alkyl, lower aralkyl, lower heterocyclylalkyl, heterocyclyl, and aryl, wherein $R^{29}$ is selected from

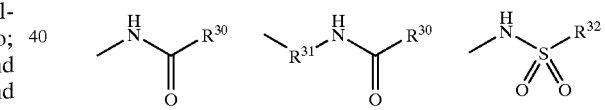

wherein $R^{30}$ is selected from lower alkyl, lower alkoxy, lower alkylamino, lower carboxyalkyl, lower alkoxyalkyl, lower alkylaminoalkyl, lower cycloalkyl, heterocyclyl, lower heterocyckylalkyl, lower heterocyclylalkoxy, lower aralkenyl, lower aralkyl, lower aralkoxy, phenyloxy, phenylamino, lower cycloalkyloxy, lower N-phenyl-N-alkylamino, lower alkylaminoalkoxy, lower alkylaminoalkylamino, lower heterocyclylalkylamino, and lower N-aralkylamino; wherein $R^{31}$ is lower alkyl; wherein $R^{32}$ is selected from lower alkyl and aryl; and wherein $R^{33}$ is selected from hydrido and lower alkyl; or a pharmaceutically-acceptable salt thereof.

Most preferred are compounds where $R^{28}$ is selected from the group consisting of methyl(phenylmethyl)amino, methyl [(4-methoxyphenyl)-methyl]amino, 1-(1,2,3,6-tetrahydropyridyl), isopropyl(methyl)amino, (4-furoyl)piperazinyl, (2-cyano)ethyl, (4-thenoyl)piperazinyl, (4-benzenesulfonyl)-piperazinyl, diisopropylamino, [methyl(4-dimethylamino)phenylmethyl]amino, methyl(2-pyridylmethyl)-amino; methyl[2-(3-indolyl)ethyl]amino, 4-morpholyl, allyl(methyl)amino, 1-decahydroquinolyl, and 4-(1-acetylpiperadinyl); and $R^{29}$ is selected from the group consisting of [(1,1-dimethylethoxy)carbonyl]amino, benzoylamino, (phenylmethoxyacetyl)amino, and (2,4,6-Trifluorobenzoyl)amino.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where used, either alone or within other terms such as "haloalkyl", "alkylsulfonyl", "alkoxyalky", "hydroxyalky" and "aralkyl" the term "alkyl" embraces linear or branched radicals having one to about twenty carbon atoms or, preferably, one to about twelve carbon atoms. More preferred alkyl radicals are "lower alkyl" radicals having one to about ten carbon atoms. Most Preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like.

The term "halo" means halogens such as fluorine, chlorine, bromine, or iodine.

The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy.

The term "alkoxyalkyl" also embraces alkyl radicals having two or more alkoxy radicals attached to the alkyl radical, that is, to form monoalkoxyalkyl and dialkoxyalkyl radicals. More preferred alkoxyalkyl radicals are "lower alkoxyalkyl" radicals having one to six carbon atoms and one or two alkoxy radicals. Examples of such radicals include methoxymethyl, methoxyethyl, ethoxyethyl, methoxybutyl and methoxypropyl. The "alkoxy" or "alkoxyalkyl" radicals may be further substituted with one or more halo atoms, such as fluoro, chloro or bromo, to provide "haloalkoxy" or haloalkoxalkyl radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one, two or three rings wherein such rings may be attached together in a pendent manner or may be fused.

The term "aryl" embraces aromatic radicals such as phenyl, naphthyl, tetrahydronaphhthyl, indane and biphenyl. Aryl moieties may also be substituted at a substitutable position with one or more substituents selected independently from alkyl, aralkyl, alkoxyalky, alkylaminoalkyl, carboxyalkyl, alkoxycarbonylalkyl, aminocarbonylalkyl, alkoxy, aralkoxy, heterocyclylalkoxy, alkylaminoalkoxy, carboxyamino, carboxyaminoalkyl, carboxyaminoaralkyl, amino, halo, nitro, alkylamino, alkylcarbonylamino, arylcarbonylamino, alkoxycarbonylamino, aralkoxycarbonylamino, aminocarbonylamino, alkylaminocabonylamino, alkylsulfonylamino, arylsulfonylamino, acyl, cyano, carboxy, aminocarbonyl, alkylaminocarbonyl, alkoxycarbonyl and aralkoxycarbonyl.

The terms "heterocyclyl", or "heterocyclic" embrace saturated, partially saturated and unsaturated heteroatom-containing ring-shaped radicals, where the heteroatoms may be selected from nitrogen, sulfur and oxygen. Examples of saturated heterocyclic radicals include saturated 5 to 7-membered heteromonocyclic group containing 1 to 4 nitrogen atoms (e.g., pyrrolidinyl imidazolidinyl, piperidinyl, piperazinyl, tropanyl, homotropanyl, etc.); saturated 5 to 7-membered heteromonocyclic group containing 1 to 2 oxygen atoms and 1 to 3 nitrogen atoms (e.g., morpholinyl, etc.); saturated 5 to 7-membered heteromonocyclic group containing 1 to 2 sulfur atoms and 1 to 3 nitrogen atoms.(e.g., thiazolidinyl, etc.).

Examples of partially saturated heterocyclic radicals include dihydrothiophene, dihydropyran, oxazolinyl, dihydrofuran and dihydrothiazole. Examples of unsaturated heterocyclic radicals, also termed "heteroaryl" radicals include unsaturated 5 to 7-membered heteromonocyclic group containing 1 to 4 nitrogen atoms, for example, pyrrolyl, pyrrolinyl, imidazolyl pyrazolyl, pyridyl,pyrimidyl, azepinyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g., 1H-tetrazolyl, 2H-tetrazolyl, etc.), etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 5 to 7-membered heteromonocyclic group containing a sulfur atom, for example, thienyl, etc; unsaturated 5 to 7 membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclic group containing 1 to 2 oxygen atoms and 1 to 3 nitrogen atoms (e.g., benzoxazolyl, benzoxadiazolyl, etc.); unsaturated 5 to 7-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclic group containing 1 to 2 sulfur atoms and 1 to 3 nitrogen atoms (e.g., benzothiazolyl, benzothiadiazolyl, etc.) and the like. The term also embraces radicals where heterocyclic radicals are fused with aryl radicals. Examples of such fused bicyclic radicals include benzofuryl, benzothienyl, and the like. Said "heterocyclyl" radicals may also be substituted at a substitutable position with one or more substituents selected independently from alkyl, aralkyl, alkoxyalkyl, alkylaminoalkyl, carboxyalkyl, alkoxycarbonylalkyl, aminocarbonylalkyl, alkoxy, aralkoxy, alkylaminoalkoxy, aminocarboxy, alkylaminocarboxy, aralkylaminocarboxy, amino, halo, nitro, alkylamino, alkylcarbonylamino, arylcarbonylamino, alkoxycarbonylamino, aralkoxycarbonylamino, aminocarbonylamino, alkylaminocarbonylamino, alkylsulfonylamino, arylsulfonylamino, acyl, cyano, carboxy, aminocarbonyl, alkoxycarbonyl and aralkoxycarbonyl. More preferred heteroaryl radicals include 5 to 6-membered heteroaryl radicals.

The term "cycloalkyl" embraces radicals having 3 to 10 carbon atoms. More preferred cycloalkyl radicals are "lower cycloalkyl" radicals having 3 to 7 carbon atoms. Examples include radicals such as cyclopropyl, cyclobutyl, cyclopentyl, cyclohexyl and cycloheptyl.

The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide "haloalkylsulfonyl" radicals. More preferred haloalkylsulfonyl radicals are "lower haloalkylsulfonyl" radicals having one or more halo atoms attached to lower alkylsulfonyl radicals as described above. Examples of such lower haloalkylsulfonyl radicals include fluoromethylsulfonyl, trifluoromethylsulfonyl, and chloromethylsulfonyl. The term "arylsulfonyl" embraces aryl radicals as defined above, attached to a sulfonyl radical. Examples of such radicals include phenylsulfonyl. The terms "sulfamyl", "aminosulfonyl" and "sulfonamidyl" denotes $NH_2O_2S$.

The terms "carboxy" or "carboxyl", whether used alone or with other terms, such as "carboxyalkyl", donotes —$CO_2H$.

The term "carbonyl", whether used alone or with other terms, such as "alkoxycarbonyl", denotes —(C=O)—. The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted and unsubstituted methoxycarbonyl, ethoxycarbonyl, propoxycarbonyl, butoxycarbonyl, and hexyloxycarbonyl.

The term "aralkyl" embraces aryl-substituted alkyl radicals. Preferable aralkyl radicals are "lower aralkyl" radicals having aryl radicals attached to alkyl radicals having 1 to 6 carbon atoms. Examples of such radicals include benzyl, diphenylmethyl, triphenylmethyl, phenylethyl and diphenylethyl. The aryl in the aralkyl may be additionally substituted as described above.

The term "aralkenyl" embraces aryl-substituted alkenyl radicals. Preferable aralkenyl radicals are "lower phenylalkenyl" radicals having phenyl radicals attached to alkenyl radicals having 1 to 6 carbon atoms. Examples of such radicals include phenylethenyl and phenylpropenyl. The aryl in said aralkyl may be additionally substituted as described above. The terms benzyl and phenylmethyl are interchangeable.

The term "alkylcarbonyl" includes radicals having alkyl radicals as defined above, attached to a carbonyl radical. More preferred alkylcarbonyl radicals are "lower alkylcarbonyl" radicals having one to six carbon atoms. Examples of such radicals include methylcarbonyl and ethylcarbonyl.

The term "carboxyalkyl" embraces radicals having a carboxy radical as defined above, attached to an alkyl radical. The alkanoyl radicals may be substituted to unsubstituted, such as formyl, acetyl, propionyl, butyryl, isobutyryl, valeryl, isovaleryl, pivaloyl, hexanoyl, trifluoroacetyl or the like, in which the preferable one is formyl, acetyl, propionyl or tribfluoroacetyl.

The term "heterocyclylalkyl" embraces heterocyclic-substituted alkyl radicals. More preferred heterocyclylalkyl radicals are "lower heterocyclylalkyl" radicals having 5 to 6 membered heterocyclyl radicals attached to lower alkyl radicals having 1 to 6 carbon atoms. Examples of such radicals include pyrrolidinylmethyl, piperidinylmethyl, morpholinylmethyl, piperazinylmethyl, oxazolylmethyl, oxazolylethyl, oxazolinylmethyl, oxazolinylethyl, indolylethyl, indolylmethyl, pyridylmethyl, quinolylmethyl, thienylmethyl, furylethyl and quinolylethyl. The heterocyclic in said heterocyclylalkyl may be additionally substituted as described above.

The term "aryloxy" embraces aryl radicals, as defined above, attached to an oxygen atom. The aryl in said aryloxy may be additionally substituted as described above. Examples of such radicals include phenoxy.

The term "aralkoxy" embraces oxy-containing aralkyl radicals attached through an oxygen atom to other radicals. The "aralkoxy" radical may be further substituted on the aryl ring portion of the radical.

The term "alkylamino" denotes amino groups which have been substituted with 1 or 2 alkyl radicals. More preferred alkylamino radicals are "lower alkylamino" having alkyl radicals of 1 to 6 carbon atoms attached to the nitrogen atom of an amine. Suitable "lower alkylamino" may be mono or dialkylamino such as N-methylamino, N-ethylamino, N,N-dimethylamino, N,N-diethylamino or the like.

The term "alkylaminoalkyl" denotes alkylamino groups, as defined above, attached to an alkyl radical. More preferred alkylaminoalkyl radicals are "lower alkylaminoalkyl" having 1 to 6 carbon atoms attached to a lower aminoalkyl radical as described above. Suitable "lower alkylaminoalkyl" may be mono or dialkylaminoalkyl radicals such as N-methylaminomethyl, N-ethylaminomethyl, N,N-dimethylaminomethyl, N,N-dimethylaminoethyl N,N-dimethylaminopropyl or the like.

The term "dialkylaminoalkyl" also includes radicals where the bridging alkyl moiety is optionally substituted with alkylsulfonyl, alkoxy, aralkoxy, heterocyclyl, and aryl.

The term "alkylaminoalkoxy" denotes alkylamino groups, as defined above, attached to an alkoxy radical. Suitable "alkylaminoalkoxy" may be mono or dialkylaminoalkoxy radicals such as N-methylaminomethoxy, N-ethylaminomethoxy, N,N-dimethylaminomethoxy, N,N-dimethylaminoethoxy N,N-dimethylaminopropoxy or the like.

The term "alkylaminocarbonyl" embraces alkylamino radicals, as described above, to a carbonyl radical. More preferred alkylaminocarbonyl radicals are "lower alkylaminocarbonyl" having lower alkylamino radicals, as described above, attached to a carbonyl radical. Examples of such radicals include N-methylaminocarbonyl and N,N-dimethylaminocarbonyl.

The term "arylamino" denotes amino groups which have been substituted with 1 or 2 aryl radicals, such as N-phenylamino. The "arylamino" radicals may be further substituted on the aryl ring portion of the radical.

The terms "N-arylaminoalkyl" and "N-aryl-N-alkyl-aminoalkyl"denote amino groups which have been substituted with one aryl radical or one aryl and one alkyl radical, respectively, and having the amino group attached to an alkyl radical. More preferred arylaminoalkyl radicals are "lower arylaminoalkyl" having the arylamino radical attached to 1 to 6 carbon atoms. Examples of such radicals include N-phenylaminomethyl and N-phenyl-N-methylaminomethyl.

The term "aminocarbonyl" denotes an amide group of the formula —$C(=O)NH^2$. The term "aminocarbonylalkyl" denotes an aminocarbonyl group attached to an alkyl radical. More preferred are "lower aminocarbonylalkyl" having lower aminocarbonyl radicals as described above attached to alkyl of one to six carbon atoms. The term "alkylaminocarbonylalkyl" denotes an aminocarbonyl group which has been substituted with one or two alkyl radicals and attached to an alkyl radical. More preferred are "lower alkylaminocarbonylalkyl" having lower alkylaminocarbonyl radicals as described above attached to alkyl radicals of one to six carbon atoms.

The term "aryloxy" embraces aryl radicals attached to a divalent oxygen atom, that is, to form monoaryloxy and diaryloxy radicals. The more preferred aryloxy radicals are "lower aryloxy". An example includes phenoxy. "Amino acid residue" means any of the naturally occurring alpha-, beta- and gamma-amino carboxylic acids, including their D and L optical isomers and racemic mixtures thereof, synthetic amino acids, and derivatives of these natural and synthetic amino acids. The amino acid residue is bonded through a nitrogen of the amino acid. The naturally occurring amino acids which can be incorporated in the present invention include, but are not limited to, alanine, arginine, asparagine, aspartic acid, cysteine, cystine, glutamic acid, glutamine, glycine, histidine, isoleucine, leucine, lysine, methionine, omithine, phenylalanine, proline, serine, threonine, thyroxin, tryptophan, tyrosine, valine, β-alanine, and γ-aminobutyric acid. Derivatives of amino acids which can be incorporated in the present invention include, but are not limited to, amino acids having protected and modified carboxylic acids, including acid esters and amides, protected amines, and substituted phenyl rings, including but not limited to alkyl, alkoxy and halo substituted tyrosine and phenylalanine.

The present invention comprises a pharmaceutical composition comprising a therapeutically-effective amount of a compound of Formula II in association with at least one pharmaceutically-acceptable carrier, adjuvant or diluent.

The present invention also comprises a method of therapeutic and prophylactic treatment of viral infections, particularly herpetoviridae infection, in a subject, the method comprising treating the subject having such herpes infection a therapeutically-effective amount of a compound of Formula II.

The present invention also comprises a method of inhibiting a viral protease, the method comprising administering a therapeutically-effective amount of a compound of Formula II.

Also included in the family of compounds of Formula II are the stereoisomers and tautomers thereof. Compounds of the present invention can possess one or more asymmetric carbon atoms and are thus capable of existing in the form of optical isomers as well as in the form of racemic or nonracemic mixtures thereof. Accordingly, some of the compounds of this invention may be present in racemic mixtures which are also included in this invention. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts.

A different process for separation of optical isomers involves the use of a chiral chromatography column optimally chosen to maximize the separation of the enantiomers. Still another available method involves synthesis of covalent diastereoisomeric molecules by reacting an amine functionality of precursors to compounds of Formula II with an optically pure acid in an activated form or an optically pure acid in an activated form or an optically pure isocyanate. Alternatively, diastereomeric derivatives can be prepared by reacting a carboxyl functionality of precursors to compounds of Formula II with an optically pure amine base. The synthesized diastereoisomers can be separated by conventional means such as chromatography, distillation, cystallization or sublimation, and then hydrolyzed to deliver the enantiomerically pure compound. The optically active compounds of Formula II can likewise be obtained by utilizing optically active starting materials. These isomers may be in the form of a free acid, a free base, an ester or a salt.

Additional methods for resolving optical isomers, known to those skilled in the art may be used, for example, those discussed by Jaques et al. in *Enantiomers, Racemates, and Resolutions*, John Wiley and Sons, New York (1981).

Also included in the family of compounds of Formula II are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula II may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyic, p-hydroxybenzoic, phenylacetic, mandelic, embonic (pamoic), methanesulfonic, ethylsulfonic, benzenesulfonic, pantothenic, toluenesulfonic, 2-hydroxyethanesulfonic, sulfanilic, stearic, cyclohexylaminosulfonic, algenic, β-hydroxybutyric, galactaric and galacturonic acid. Suitable pharmaceutically-acceptable base addition salts of compounds of Formula II include metallic salts made from aluminum, calcium, lithium, magnesium, potassium, sodium and zinc or organic salts made from N,N'-dibenzylethylenediamine, choline, chloroprocaine, diethanolamine, ethylenedianine, meglumine (N-methylglucamine) and procaine. All of these salts may be prepared by conventional means from the corresponding compound of Formula II by reacting, for example, the appropriate acid or base with the compound of Formula II.

Also embraced within this invention is a class of pharmaceutical compositions comprising one or more compounds of Formula II in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for sample, be administered orally, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably between about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut, oil, sesame oil, benzyl alcohol, sodium chloride, and/or various buffers. Other adjuvants and modes of administration are well and widely known in the pharmaceutical art.

For infections of the eye or other external tissues, e.g., mouth and skin, the formulations are preferably applied as a topical ointment or cream containing the active ingredient (s) in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in water cream base. If desired, the aqueous phase of the cream base may include, for example, at least 30% w/w of a polyhydric alcohol such as propylene glycol, butane-1,3-diol, mannitol, sorbitol glycerol, polyethylene glycol and mixtures thereof The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations in very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-thylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiviral active ingredients are preferably present in such formulations in a concentration of 0.5 to 20%, advantageously 0.5 to 10% and particularly about 1.5% w/w.

EXAMPLES

The following examples contain detailed descriptions of the methods of preparation of compounds of Formula II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

The following abbreviations are used:

| | |
|---|---|
| EtOAc | ethyl acetate |
| HCl | hydrochloric acid |
| DMSO | dimethylsulfoxide |
| $d_6$-DMSO | deuterated dimethylsulfoxide |
| $CDCl_3$ | deuterated chloroform |
| $CHCl_3$ | chloroform |
| $CD_3OD$ | deuterated methanol |
| $Et_2O$ | diethyl ether |
| $MgSO_4$ | magnesium sulfate |
| $H_2SO_4$ | sulfuric acid |
| $NaHCO_3$ | sodium bicarbonate |
| $KHSO_4$ | potassium hydrogen sulfate |
| NMM | N-methylmorpholine |
| DMF | dimethylformamide |
| DMAP | 4-dimethylaminopyridine |
| CDI | carbonyldiimidazole |
| NaOH | sodium hydroxide |
| KOH | potassium hydroxide |
| LiOH | lithium hydroxide |
| $Pd(OH)_2$/C | palladium hydroxide on carbon |
| Pd/C | palladium on carbon |
| EDC | 1-(3-dimethylaminopropyl)-3-ethylcarbodiimide-HCl |
| BOC | tert-butyloxycarbonyl |
| TLC | thin layer chromatography |
| MeOH | methanol |
| KI | potassium iodide |
| $CH_2Cl_2$ | methylene chloride |

The following is a list of inventive compounds and comparative compounds.

| Compound | Formula |
|---|---|
| 1 | 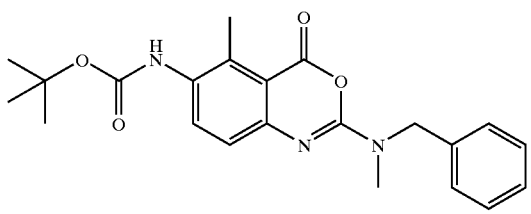 |
| 2 | 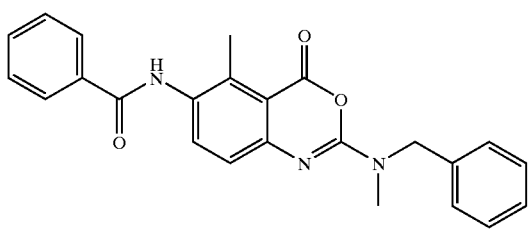 |
| 3 | 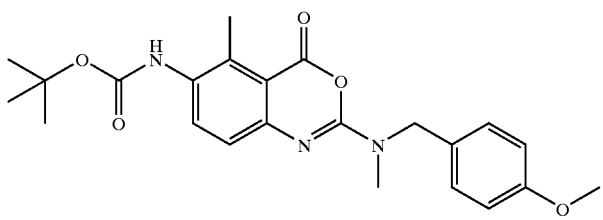 |
| 4 | 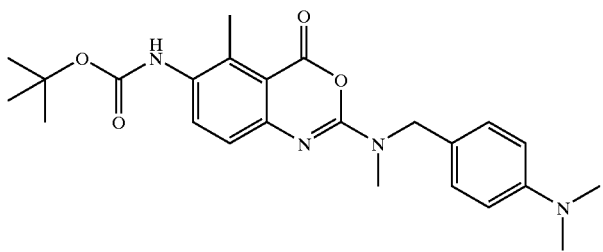 |
| 5 | 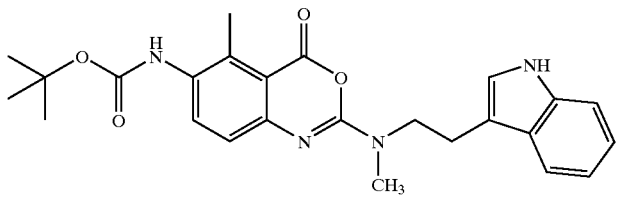 |
| 6 | 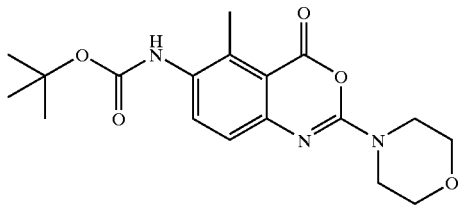 |

-continued
| | |
|---|---|
| 7 | 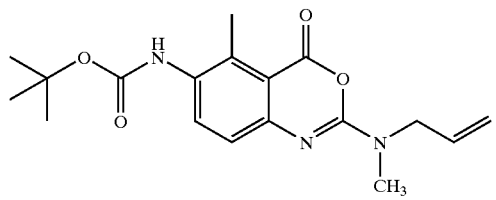 |
| 8 | 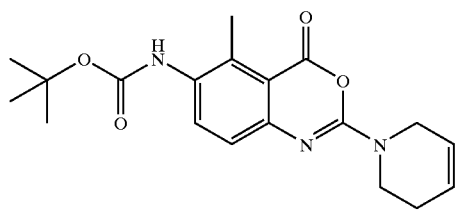 |
| 9 | 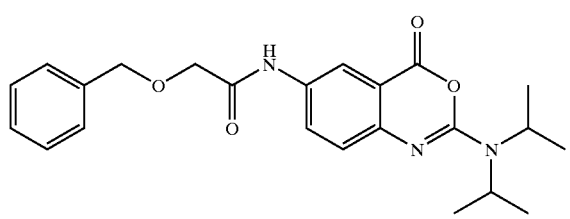 |
| 10 | 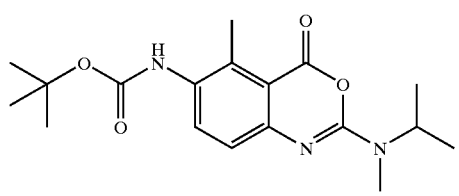 |
| 11 | 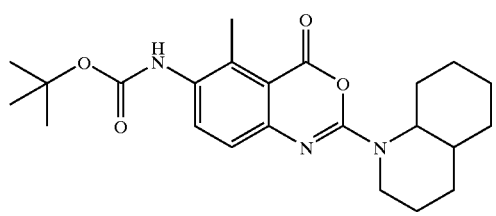 |
| 12 | 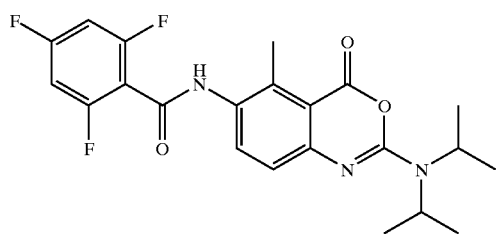 |
| 13 | 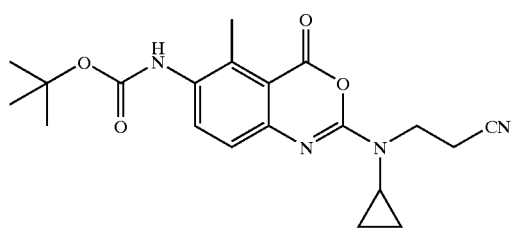 |

-continued
| | |
|---|---|
| 14 | 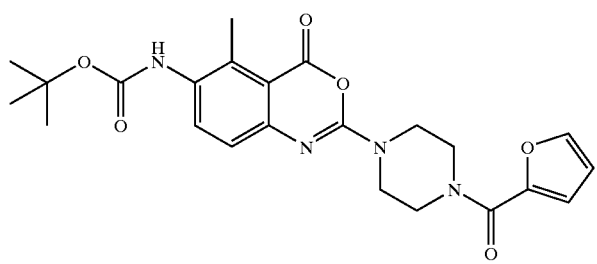 |
| 15 | 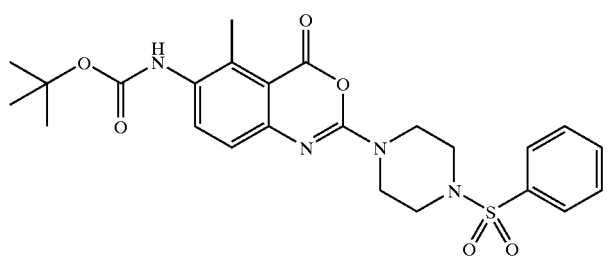 |
| 16 | 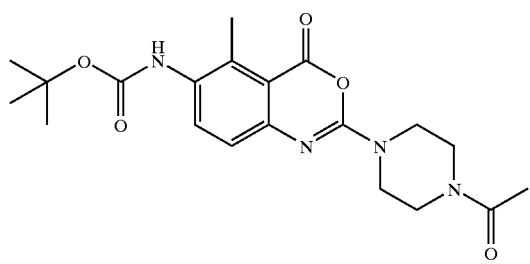 |
| 17 | 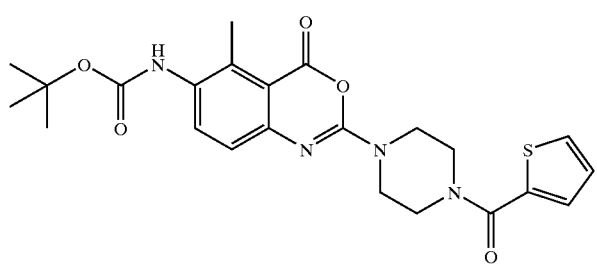 |
| 18 | 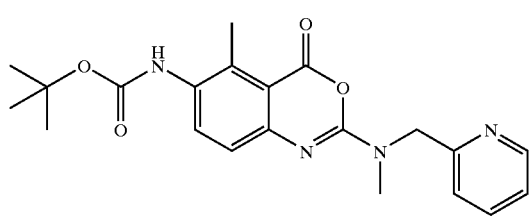 |
| Comparative Compound | Formula |
|---|---|
| CC 1 | 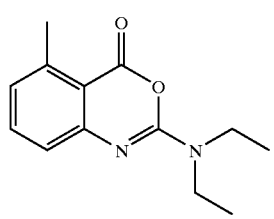 |

| | |
|---|---|
| CC 2 | 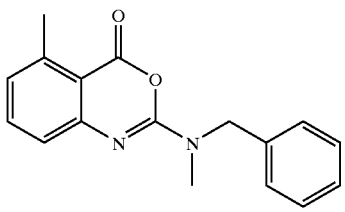 |
| CC 3 | 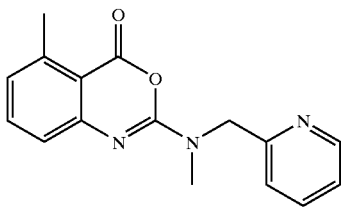 |
| CC 4 | 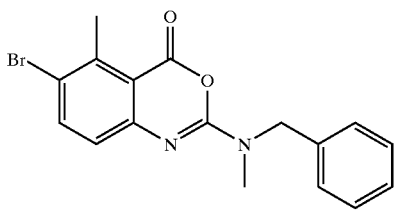 |
| CC 5 | 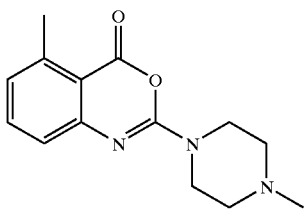 |
| CC 6 | 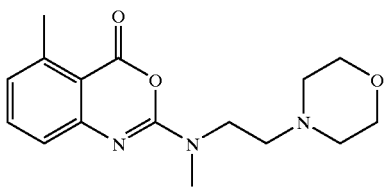 |

Example 1

Compound 1

6-[[(1,1-Dimethylethoxy)carbonyl]amino]-5-methyl-2-[methyl(phenylmethyl)amino]-4H-3,1-benzoxazin-4-one A. Preparation of 3-[[(1,1-dimethylethoxy)carbonyl]amino]-2-methyl-6-[[[methyl(phenylmethyl)-amino]carbonyl]amino]benzoic acid, 2-(trimethylsilyl)ethyl ester.

To a solution of 6-amino-3-[[(1,1-dimethylethoxy)carbonyl]amino]-2-methylbenzoic acid, 2-(trimethylsilyl)ethyl ester (0.11 mmol in 3ml of $CH_2Cl_2$), was added a solution of p-Nitrophenyl chloroformate (0.1 mmol, 20.2 mg) in $CH_2Cl_2$(0.2 ml). After stirring at room temperature for 3 hours, resulting solution was washed with 1N-HCl, water, and dried over $MgSO_4$. To this solution of activated carbamate, methyl(phenylmethyl)amine (0.016 ml, 0.12 mmol) was added. After stirring at room temperature for 15 hours, a solution of tetrafluoroplthalic anhydride (15 mg, 0.07 mmol) in $CH_2Cl_2$(0.7 ml) was added and stirred for 3 hours, followed by polyamine resin prepared by the method of L. Flynn et al. (J. Amer. Chem. Soc., 119, 4874–4881 (1997)) (200 mg, 0.6 mmol). After 1 hour, the mixture was filtrated and concentrated, dissolved in $CH_2Cl_2$ again, Amberlyst A-21 (50 mg) was added, stirred for 1 hour. Resin was removed with filtration, the solution was concentrated to afford white crystal (38.7 mg) $^1$H-NMR (270 MHz, $CDCl_3$) δ 0.06(s, 9H), 1.0–1.1(m, 2H), 1.50(s, 9H), 2.28(s, 3H), 2.99(s, 3H), 4.3–4.4(m, 2H), 4.59(s, 2H), 6.15(br.s, 1H), 7.2–7.3(m, 5H), 7.67(br.d, 1H, J=9 Hz), 8.01(d, 1H, J=9 Hz), 8.25(s, 1H), HPLC(A) retention time=26.8 min.

B. Preparation of 3-[[(1,1-dimethylethoxy)carbonyl]amino]-2-methyl-6-[[[methyl(phenylmethyl)-amino]carbonyl]amino]benzoic acid.

To a solution of the product of step A(38.7 mg) in 3 ml of THF was added a solution of TBAF in TBF (1.0 M, 0.12 ml, 0.12 mmol) and stirred at room temperature for 1 hour. Amberlyst A-15 H form (200 mg), Amberlyst A-15 calcium form (200 mg) were added, shaken overnight, filtrated, and concentrated to afford white crystal (26.0 mg). $^1$H-NMR (270 MHz, $CD_3OD$) δ 1.42(s, 9H), 2.24(s, 3H), 2.89(s, 3H), 4.50(s, 2H), 7.1–7.3(m, 6H), 7.64(d, 1H, J=9 Hz), HPLC(A) retention time=15.4 min.

C. 6-[[(1,1-Dimethylethoxy)carbonyl]amino]-5-methyl-2-[methyl(phenylmethyl)-amino]-4H-3,1-benzoxazin-4-one To a solution of the product of step B(26.0 mg) in 4 ml of DMF was added P-EDC (300 mg, 0.3 mmol), stirred for 2 hours. Filtrated, concentrated to afford white crystal (21.5 mg). $^1$H-NMR (270 MHz, CDCl$_3$) δ 1.51(s, 9H), 2.65(s, 3H), 3.08(s, 3H), 4.74(s, 2H), 6.26(br.s, 1H), 7.12(d, 1H, J=9 Hz), 7.2–7.4(m, 5H), 7.83(br.d, 1H), HPLC(A) retention time=24.7 min, MS(MH+)=396.

A similar method was used to prepare the following compounds

Compound 3

6-[[(1,1-Dimethylethoxy)carbonyl]amino]-5-methyl-2-[methyl[(4-methoxyphenyl)methyl]amino]4H-3,1-benzoxazin-4-one $^1$H-NMR (270 MHz, CDCl$_3$) δ 1.51(s, 9H), 2.65(s, 3H), 3.06(s,3H), 3.80(s, 3H), 4.67(s, 2H), 6.23(br.s, 1H), 6.87(d, 2H, J=9 Hz), 7.12(d, 1H, J=9 Hz), 7.25(d, 2H, J=9 Hz), 7.83(br.d, 1H), HPLC(B) retention time=8.26 min, MS(MH+)=426.

Compound 8

6-[[(1,1-Dimethylethoxy)carbonyl]amino]-5-methyl-2-[1-(1,2,3,6-tetrahydro-pyridyl)]-4H-3,1-benzoxazin-4-one HPLC(A) retention time=18.4 min, MS(MH+)=358.

Compound 10

6-[[(1,1-Dimethylethoxy)carbonyl]amino]-5-methyl-2-[isopropyl(methyl)amino]-4H-3,1-benzoxazin-4-one HPLC(A) retention time=22.9 min.

Compound 14

6-[[(1,1-Dimethylethoxy)carbonyl]amino]-5-methyl-2-[(4-furoyl)piperazinyl]-4H-3,1-benzoxazin-4-one HPLC(A) retention time=20.0 min.

Compound 13

6-[[(1,1-Dimethylethoxy)carbonyl]amino]-5-methyl-2-[(2-cyanoethyl)-(cyclopropyl)amino]-4H-3,1-benzoxazin-4-one HPLC(A) retention time=21.0 min.

Compound 17

6-[[(1,1-Dimethylethoxy)carbonyl]amino]-5-methyl-2-[(4-thenoyl)piperzinyl]-4H-3,1-benzoxazin-4-one HPLC(B) retention time=7.02 min.

Compound 15

6-[[(1,1-Dimethylethoxy)carbonyl]amino]-5-methyl-2-[(4-benzenesulfonyl)-piperazinyl]-4H-3,1-benzoxazin-4-one HPLC(B) retention time=7.88 min.

Example 2

Compound 2

6-(benzoylamino)-5-methyl-2-[methyl(phenylmethyl)amino]-4H-3,1-benzoxazin-4-one

A. Preparation of 3-amino-2-methyl-6-[[[methyl(phenylmethyl)amino]-carbonyl]amino]-benzoic acid, 2-(trimethylsilyl)ethyl ester.

To a solution of the product of example 1-step A (40.2 mg) in 1,4-doixane (2 ml) was added 4N-HCl solution in 1,4-dioxane (2 ml). After stirred at room temperature for 2 hours, the reaction mixture was concentrated. CH$_2$Cl$_2$ (4 ml) and DMF (0. 5 ml) was added, dissolved, and Amberlyst A-21 (100 mg) was added. Shaken for 1 hour, the resin was filtered off, concentrated to afford 35.7 mg of product. $^1$H-NMR (270 MHz, CDCl$_3$) δ 0.06(s, 9H), 0.9–1.0(m, 2H), 2.18(s, 3H), 3.97(s, 3H), 4.2–4.3(m, 2H), 4.58(s, 2H), 6.79 (d, 1H, J=8.9 Hz), 7.2–7.4(m, 5H), 7.77(d, 1H, J=8.9 Hz), 8.14(s, 1H), HPLC(A) retention time=23.4 min.

B. Preparation of 3-(benzoylamino)-2-methyl-6-[[[methyl(phenylmethyl)amino]-carbonyl]amino]-benzoic acid, 2-(trimethylsilyl)ethyl ester.

To a solution of the product of step A (35.7 mg) in 2 ml of CH$_2$Cl$_2$were added pyridine (0.011 ml, 0.14 mmol), benzoyl chloride (0.014 ml, 0.12 mmol). After stirring at room temperature for 14 hours, polyamine resin (200 mg, 0.6 mmol) was added, stirred for 2 hours. Filtration and concentration afforded 32.3 mg of the product. $^1$H-NMR (270 MHz, CDCl$_3$) δ 0.06(s, 9H), 1.0–1.1 (m, 2H), 2.33(s, 3H), 2.98(s, 3H), 4.2–4.3(m, 2H), 4.57(s, 2H), 7.2–7.6(m, 9H),7.8–7.9(m, 3H), 8.07(d, 1H, J=9 Hz), 8.84(s, 1H), HPLC(A) retention time=25.4 min.

C. Preparation of 3-(benzoylamino)-2-methyl-6-[[[methyl(phenylmethyl)-amino]-carbonyl]amino]-benzoic acid.

To a solution of the product of step B (32.3 mg) in 3 ml of THF was added a solution of TBAF in THF (1.0 M, 0.12 ml, 0.12 mmol) and stirred at room temperature for 1 hour. Amberlyst A-15 H form (200 mg), Amberlyst A-15 calcium form (200 mg) were added, shaken overnight, filtrated, and concentrated to afford white crystal (25.4 mg). $^1$H-NMR (270 MHz, CDCl$_3$) δ 2.19(s, 3H), 2.90(s, 3H), 4.52(s, 2H), 7.2–7.5(m, 7H), 7.77(d, 1H, J=9 Hz), 7.9(m, 2H), 8.58(s, 1H), 8.96(br.s, 1H).

D. 6-(benzoylamino)-5-methyl-2-[methyl(phenylmethyl)amino]-4H-3,1-benzoxazin-4-one.

To a solution of the product of step C (25 mg) in 4ml of DMF was added P-EDC (300 mg, 0.3 mmol), stirred for 2 hours. Filtrated, concentrated to afford white crystal (15.8 mg). $^1$H-NMR (270 MHz, CDCl$_3$)δ 2.69(s, 3h), 3.01(s, 3H), 4.75(s, 2H), 7.16(d, 1H, J=9 Hz), 7.2–7.6(m, 8H), 7.8–8.0 (m, 4H), HPLC(A) retention time=22.4 min. MS(MH+)=400.

Compound 9

6-[(Phenylmethoxyacetyl)amino]-5-methyl-2 (diisopropylamino)-4H-3,1-benzoxazin-4one HPLC(A) retention time=24.1 min.

Compound 12

6-[(2,4,6-Trifluorobenzoyl)amino]-5-methyl-2 (diisopropylamino)-4H-3,1-benzoxazine-4-one HPLC(A) retention time=23.3 min.

Example 3

Compound 4

6-[[(1,1-Dimethylethoxy)carbonyl]amino]-5-methyl-2-[[[4-(dimethylamino)phenyl]methyl] methylamino]-4H-3,1-benzoxazin-4-one A. Preparation of 3-[[(1,1-dimethylethoxy)carbonyl] amino]-2-methyl-6-[[[N-[[4-(dimethylamino)phenyl] methyl]methylamino]carbonyl]amino]benzoic acid, 2-(trimethylsilyl)ethyl ester.

Proceeding in a manner similar to example 1A, substituting methyl(phenylmethyl)amine with N-[(4-dimethylamino)phenyl]methyl]methylamine. $^1$H-NMR(270 MHz, CDCl$_3$) d 0.06(s, 9H), 1.0–1.1(m, 2H), 1.50(s, 9H), 2.28(s, 3H), 2.93 (s, 9H), 4.2–4.3(m, 2H), 4.48(s, 2H), 6.11(br.s, 1H), 6.70(d, 2H,J=9 Hz), 7.19(d, 2H, J=9 Hz), 7.58(br.d, 1H), 8.06(d, 1H, J=9 Hz), 8.62(br. S, 1H).

B. Preparation of 6-[[(1,1-Dimethylethoxy)carbonyl]amino]-5-methyl-2-[[[4-(dimethylamino)phenyl]methyl]methylamino]-4H-3,1-benzoxazin-4-one.

To a solution of the product of step A (521 mg, 0.935 mmol) in 10 ml of THF, was added a solution of tetrabutylammonium fluoride in THF (1.0 M, 1.12 ml, 1.12 mmol). Stirred at room temperature for 45 min., acetyl chloride (0.12 ml, 1.7 mmol) was added, and stirred for 1.5 hours. Concentrated, purified over silica gel, washed with saturated NaHCO$_3$ aqueous solution to afford white amorphous solid (241 mg). $^1$H-NMR (270 MHz, CDCl$_3$) d 1.51(s, 9H), 2.65(s, 3H), 2.93(s, 6H), 3.11(s, 3H), 4.63(s, 2H), 6.21(br.s, 1H), 6.69(d, 2H, J=9 Hz), 7.12(d, 1H, J=9 Hz), 7.19 (d, 2H, J=9 Hz), 7.82(br.d, 1H, J=9 Hz), HPLC(B) retention time= 8.62 min, MS(MH+)=439.

Compound 18

6-[[(1-Dimethylethoxy)carbonyl]amino]-5-methyl-2-[methyl(2-pyridylmethyl)-amino]-4H-3,1-benzoxazin-4-one HPLC(B) retention time=6.71 min., MS(MH+)=397.

Compound 5

6-[[(1-Dimethylethoxy)carbonyl]amino]-5-methyl-2-[methyl[2-(3-indolyl)ethyl]amino]-4H-3,1-benzoxazin-4-one $^1$H-NMR (270 MHz, CDCl$_3$)δ 1.52(s, 9H), 2.65(s, 3H), 3.1(m, 5H), 3.82(t, 2H, J=7 Hz), 6.21(br.s, 1H), 7.0–7.4(m, 4H), 7.7–8.1(m, 3H). HPLC(B) retention time=8.08 min., MS(MH$^+$)=449.

Compound 6

6-[[(1,1-Dimethylethoxy)carbonyl]amino]-5-methyl-2-(4-morpholyl)-4H-3,1-benzoxazin-4-one $^1$H-NMR (270 MHz, CDCl$_3$) δ 1.52(s, 9H), 2.65(s, 3H), 3.72(d, 4H, J=3 Hz), 3.75(d, 4H, J=3 Hz), 6.25(br.s, 1H), 7.19(d, 1H, J=9 Hz), 7.86(br.d, 1H, J=9 Hz).

HPLC(B) retention time=5.84min., MS(MH$^+$)=362.

Compound 7

6-[[(1,1-Dimethylethoxy)carbonyl]amino]-5-methyl-2-[allyl(methyl)amino]-4H-3,1-benzoxazin-4-one $^1$H-NMR (270 MHz, CDCl$_3$) δ 1.41(s, 9H), 2.44(s, 3H), 2.99(s, 3H), 4.06(d, 2H, J=5 Hz), 5.1–5.3(m, 2H), 5.7–6.0 (m, 1H), 6.98(d, 1H, J=9 Hz), 7.44(d, 1H, J=9 Hz), 8.68(br.s, 1H). HPLC(A) retention time=21.88 min., MS(MH$^+$)=346.

Compound 11

6-[[(1,1-Dimethylethoxy)carbonyl]amino]-5-methyl-2-(decahydroquinolyl)-4H-3,1benzoxazin-4-one HPLC(B) retention time=8.63min., MS(MH$^+$)=414.

Compound 16

6-[[(1,1-Dimethylethoxy)carbonyl]amino]-5-methyl-2-[4-(1-acetylpiperadinyl)]-4H-3,1-benzoxazin-4-one HPLC(B) retention time=4.98 min., MS(MH$^+$)=403.

Biological Evaluation

The compounds of this invention exhibited antiviral activity as indicated by inhibition in vitro of herpesvirus protease and HCMV infectivity. The antiviral activity of the compounds of this invention illustrated in the Examples was determined by the following methods.

Enzymatic Assay for HSV-1 Protease (Assemblin) Inhibition

FP Assay

Assemblin protease activity was determined using fluorescence polarization (FP). The fluorescent substrate was biotin-gamma-aminobutyrate -HTYLQASERFRIK-DTAF, based on the HSV-1release cleavage site. Incubation of this substrate with assemblin resulted in cleavage between alanine and serine. A change in molecular size of fluorescent substrate molecule, which was increased using avidin as a reaction stop reagent, allowed cleavage to be measured by FP. Potential protease inhibitors were dissolved in DMF and then diluted 5-fold in assay buffer. 6.5uL were added to the wells of a 96-well plate (U-bottom 96-well black plate, Dynatech or Costar) which was previously blocked using blocking solution (10 mM Tris-HCl pH 8.0, 150 mM NaCl, 0.05% Tween 20, 1 mg/mL BSA). The enzyme was diluted to 21.3 ug/mL in assay buffer (1M NaCitrate, 50 mM NaPhosphate, pH 7.4, 100mM NaCl, 20% glycerol, 2 mM TECP) and 48.5 uL were added to each well. Following a 30 minute incubation at room temperature, 10 uL of 62.5 ug/mL substrate were added. After about 90 minute incubation at room temperature, 50 uL of 2 mg/mL avidin in phosphate buffer (50 mM Naphosphate, 100 mM NaCl, pH 7.4) were added to each well. The plates were read by a fluorescence polarization plate reader. Inhibitor potency was determined by comparison with incubations lacking inhibitor.

HPLC assay

Assays were performed with the peptide substrate H-His-Thr-Tyr-Leu-Gln-Ala-Ser-Glu-Lys-Phe-Lys-Met-Trp-Gly-NH$_2$ (Bachem). This substrate is a HSV-1-amide UL26 Open Reading Frame (242–255) and is derived from the release site of HSV-1 protease. HSV-1protease cleaves between alanine and serine. The product SEKFMWG was quantified on HPLC using fluorescence detection of tryptophan residue. Enzyme was diluted to 4.3 ug/mL in assay buffer (1 M NaCitrate, 50 mM NaPhosphate, pH 7.3, 100 mM NaCl, 20% glycerol, 2 mM TCEP) and 48.5 uL were added to the tubes. Potential protease inhibitors were dissolved in DMF and then diluted 10-fold in assay buffer. 6.5 uL of inhibitor solution were added to each tube. Following a 30-minute incubation at room temperature, 10 uL of substrate in phosphate buffer (50 mM Naphosphate, 100 mM NaCl, pH 7.4) were added to all tubes. The final concentration of the substrate in the reaction mixtures was 10 uM. After a 15-minute incubation at room temperature, assays were quenched using 50 uL of 50% TCA. Inhibitor potency was determined by comparison with incubations lacking inhibitor, which under these conditions gave about 20% cleavage of substrate.

Assay Components

Recombinant HSV-1 Protease

HSV-1 protease was purified from baculovirus expressing a DNA construction encoding residues 1–288 of HSV-1 UL26 open reading frame and 32 heterologous amino acid. The construction also encoded six additional histidine residues at the amino terminus of the protease. These additional histidine residues provided an affinity ligand by which the protein was purified using Ni-NTA agarose gel (Qiagen). The purified protease was stored in stock solution (20 mM HEPES buffer, pH 8.5, containing 20% (v/v) glycerol). This stock was diluted with assay buffer to adequate concentration of enzymatic assay.

Substrate

FP Assay

A specific substrate was synthesized based on the cleavage specificity of HSV-1 protease at the "release site" of the assembly protein (DiIanni, C. L., et al., *J. Biol. Chem.* 268, 2048, (1993)). The assembly protein release site has the sequence, HTYLQA*SEKFKMWG. The substrate used was biotin-gamma -aminobutyrate-HTYLQA*SERFRIK-DTAF which was prepared by standard peptide synthetic methods such as that described in Bodansky and Bodansky, "The Practice of Peptide Synthesis" (1984), and was stored as a stock solution at 2.5 mg/mL in DMF. This was diluted to 62.5 ug/mL with phosphate buffer (50 mM Naphosphate, 100 nM NaCl, pH 7.4) just before use.

HPLC assay

The substrate was HSV-1-amide UL 26 Open Reading Frame (242–255), obtained from Bachem (Product No. M-2160).

Assay Buffer

An assay buffer (1 M NaCitrate, 50 mM NaPhosphate, pH 7.4, 100 mM NaCl, 20% glycerol, 2 mM TCEP) was used to dilute stock solutions of enzyme and inhibitors.

Antiviral and Cytotoxic Assay

These complimentary assays tested the ability of a compound to inhibit the production of new virus and the toxicity of the compound to the host cells. It was important that both assays be performed simultaneously in order to compare the results directly since toxicity may indirectly reduce viral replication.

Abbreviations:

DMEM—Dulbecco's Modified Eagle Medium; commercially available.

FBS—fetal bovine serum; commercially available and unknown factors necessary for growth of cells in culture.

HSV—herpes simplex virus.

Antiviral assay

The antiviral assay was estimated by plaque reduction assay performed by following methods. $1 \times 10^5$ of vero cells (African green monkey kidney cell) in 48-well plates were over-night cultured and the medium of this culture was replaced with 200 μl of 2% FBS DMEM containing 2× the desired final cordon of test compounds or no compound as control. The cultures were added 50 μl of 2% FBS DMEM containing with about 50 plaque forming units of HSV-1and next 250 μl of 2% FBS DMEM containing 1% methylcellulose. These infected cultures were incubated at 37° C., 5% $CO_2$ for 3 days until plaques was visible. The cells were fixed and stained simultaneously with 0.025% crystalviolet in 5% formalin solution and plaque were counted. The concentration of test compound which conferred 50% inhibition of plaque formation compared to no compound control was interpolated from the observed data and defined as $IC_{50}$. Results are included in Table 2.

Cytotoxic assay $4+10^4$ of vero cells in 96-wells were over-night cultured in 100 μl of 10% FBS DMEM. These cultured cells were added 100 μl of 10% FBS DMEM containing 50 μM of test compounds or no compound as control. Cells were cultured incubated at 37° C., 5% $CO_2$ for 3 days. For measuring proliferation of the cells, cells were added 20 μl of alamarBlue™ and incubated for 8 hours until the color of control was changed. And then the cells were road spectrophotometically (absorbance at 570 nm and 600 nm) with BIO-RAD model 3550 microplate reader. The result was indicted as the ratio at 50 μM compound concentration and no compound.

Chymotripsin Assay

The chymotripsin assay was modified from the method of Delmar, et al. (Anal. Biochem. 99, 316–320 (1979)). Bovine pancreas α-chymotripsin(type II, Sigma) was dissolved in 0.001 N HCl at 1 mg/ml and further diluted 1/1000 in assay buffer (0.1 M Tris, pH 7.8 containing 0.1 M $CaCl_2$) before use. 0.75 μl of test compound in DMF (or DMF alone), 50 μl of assay buffer and 50 μl of enzyme were added to 96 wells plates, mixed and pre-incubated for 30 minutes at ambient temperature. Reaction was initiated by addition of 50 μl of 0.2 mM N-succinyl-Ala-Ala-Pro-Phe-p-nitroanilide (Sigma; 2 mM in DMSO diluted 1/10 in assay buffer before use). The increase in absorbance at 405 nm was monitored for 3 minutes with BIO-RAD model 3550 microplate-reader.

Human Leukocyte Elastase Assay

Human leukocyte elastase (HLE) (CALBIOCHEM) was dissolved in saline at 1 mg/ml and further diluted 1/10 in assay buffer (0.2 M Tris, pH 8.0) before use.

0.75 μl of test compound in DMF (or DMF alone), 50 μl of assay buffer and 50 μl of enzyme were added to 96 well plate, mixed and pre-incubated for 30 minutes at ambient temperature. Reaction was initiated by addition of 50 μl of 2.5 mM methoxysuccinyl-Ala-Ala-Pro-Val-p-nitroanilide (Sigma; 25 mM in DMSO diluted 1/10 in assay buffer before use). The increase in absorbance at 405 nm was monitored for 3 min. with BIO-RAD model 3550 microplate reader.

HPLC condition A

Column: YMC-Pack ODS A-312 6.0×150 mm

Eluent system:

| Time(min) | 0 | 20 | 30 |
|---|---|---|---|
| MeCN (%) | 5 | 100 | 100 |
| 10 mMNaH$_2$PO$_4$aq. | 95 | 0 | 0 |

Detection UV 254 nm

Flow rate 1.0 ml/min condition B

Column: COSMOSIL 3Cl8 4.6×50 mm

Eluent system:

| Time(min) | 0 | 5 | 15 |
|---|---|---|---|
| MeCN (%) | 30 | 90 | 90 |
| 10 mMNaH$_2$PO$_4$aq. | 70 | 10 | 10 |

Detection UV 254 nm

Flow rate 1.0 ml/min.

| | | | INHIBITION AT 50 μM | |
|---|---|---|---|---|
| COMPOUND | ENZYME IC50 (μM) | ANTIVIRUS EC50 (μM) | HLE (%) | CHYMOTRYPSIN (%) |
| 1 | 0.6 | 1.1 | 32 | 13 |
| 2 | 0.7 | 4.6 | 26 | 7 |
| 3 | 0.6 | 0.16 | 0 | 0 |
| 4 | 1.3 | 0.05 | 0 | 0 |
| 5 | 3.5 | 3.2 | 0 | 13.1 |
| 6 | 3.7 | 2.9 | 0 | 0 |
| 7 | 3.4 | 4.1 | 0 | 6.9 |
| 8 | 5 | 3.3 | 0 | 0 |
| 9 | 1.5 | 11.2 | 18.2 | 28.4 |
| 10 | 7.8 | 3.3 | 0 | 0 |

-continued

| COMPOUND | ENZYME IC50 ($\mu$M) | ANTIVIRUS EC50 ($\mu$M) | INHIBITION AT 50 $\mu$M | |
|---|---|---|---|---|
| | | | HLE (%) | CHYMOTRYPSIN (%) |
| 11 | 5.5 | 2.8 | 0 | 0 |
| 12 | 6.3 | 6.8 | 13.4 | 22.4 |
| 13 | 3.9 | 7.6 | 0 | 2.2 |
| 14 | 2 | 1.6 | 46.3 | 0 |
| 15 | 1.7 | 2.8 | 0 | 0 |
| 16 | 2.3 | 3.6 | 1.4 | 0 |
| 17 | 4.2 | 4.1 | 0 | 0 |
| 18 | 1.5 | 15.1 | 28.7 | 0 |
| CC1 | 20.0 | no data | no data | no data |
| CC2 | 3.2 | 7.5 | 101 | 101 |
| CC3 | 3.2 | 48.9 | 100 | 100 |
| CC4 | no data | 15.0 | 98 | 102 |
| CC5 | 28.0 | >50 | 100 | 98 |
| CC6 | 11.8 | >50 | 99 | 97 |

It will be apparent to those skilled in the art that various modifications and variations can be made in the compositions and methods of the present invention without departing from the spirit or scope of the invention. Thus, it is intended that the present invention cover the modifications and variations of this invention provided they come within the scope of the appended claims and their equivalents.

What is claimed is:

1. A compound selected from compounds and their pharmaceutically-acceptable salts, of the group consisting of:

6-[[(1,1-Dimethylethoxy)carbonyl]amino]-5-methyl-2-[methyl(phenylmethyl)-amino]-4H-3,1-benzoxazin-4-one;

6-[[(1,1-Dimethylethoxy)carbonyl]amino]-5-methyl-2-[methyl[(4-methoxyphenyl)-methyl]amino]-4H-3,1-benzoxazin-4-one;

6-[[(1,1-Dimethylethoxy)carbonyl]amino]-5-methyl-2-[1-(1,2,3,6-tetrahydro-pyridyl)]-4H-3,1-benzoxazin-4-one;

6-[[(1,1-Dimethylethoxy)carbonyl]amino]-5-methyl-2-[isopropyl(methyl)amino]-4H-3,1-benzoxazin-4-one;

6-[[(1,1-Dimethylethoxy)carbonyl]amino]-5-methyl-2-[(4-furoyl)piperazinyl]-4H-3,1-benzoxazin-4-one;

6-[[(1,1-Dimethylethoxy)carbonyl]amino]-5-methyl-2-[[(2-cyano)ethyl]-(cyclopropyl)amino]-4H-3,1-benzoxazin-4-one;

6-[[(1,1-Dimethylethoxy)carbonyl]amino]-5-methyl-2-[(4-thenoyl)piperazinyl]-4H-3,1-benzoxazin-4-one;

6-[[(1,1-Dimethylethoxy)carbonyl]amino]-5-methyl-2-[(4-benzenesulfonyl)-piperazinyl]-4H-3,1-benzoxazin-4-one;

6-(benzoylamino)-5-methyl-2-[methyl(phenylmethyl)amino]-4H-3,1-benzoxazin-4-one;

6-[(phenylmethoxyacetyl)amino]-5-methyl-2-(diisopropylamino)-4H-3,1-benzoxazin-4-one;

6-[(2,4,6-Trifluorobenzoyl)amino]-5-methyl-2-(diisopropylamino)-4H-3,1-benzoxazin-4-one;

6-[[(1,1-Dimethylethoxy)carbonyl]amino]-5-methyl-2-[[methyl(4-dimethylamino)-phenylmethyl]-amino]-4H-3,1-benzoxazin-4-one;

6-[[(1,1-Dimethylethoxy)carbonyl]amino]-5-methyl-2-[methyl(2-pyridylmethyl)-amino]-4H-3,1-benzoxazin-4-one;

6-[[(1,1-Dimethylethoxy)carbonyl]amino]-5-methyl-2-[methyl[2-(3-indolyl)ethyl]amino]-4H-3,1-benzoxazin-4-one;

6-[[(1,1-Dimethylethoxy)carbonyl]amino]-5-methyl-2-(4-morpholyl)-4H-3,1-benzoxazin-4-one;

6-[[(1,1-Dimethylethoxy)carbonyl]amino]-5-methyl-2-[allyl(methyl)amino]-4H-3,1-benzoxazin-4-one;

6-[[(1,1-Dimethylethoxy)carbonyl]amino]-5-methyl-2-(1-decahydroquinolyl)-4H-3,1-benzoxazin-4-one; and 6-[[(1,1-Dimethylethoxy)carbonyl]amino]-5-methyl-2-[4-(1-acetylpiperadinyl)]-4H-3,1-benzoxazin-4-one.

2. A pharmaceutical composition comprising a therapeutically-effective amount of a compound of claim 1 and a pharmaceutically acceptable carrier or diluent.

3. A method or therapeutic or prophylactic treatment of Herpes Simplex Virus in a subject, said method comprising treating said subject with an effective amount of a compound selected from compounds and their pharmaceutically-acceptable salts, of the group consisting of:

6-[[(1,1-Dimethylethoxy)carbonyl]amino]-5-methyl-2-[methyl(phenylmethyl)-amino]-4H-3,1-benzoxazin-4-one;

6-[[(1,1-Dimethylethoxy)carbonyl]amino]-5-methyl-2-[methyl[(4-methoxyphenyl)-methyl]amino]-4H-3,1-benzoxazin-4-one;

6-[[(1,1-Dimethylethoxy)carbonyl]amino]-5-methyl-2-[1-(1,2,3,6-tetrahydro-pyridyl)]-4H-3,1-benzoxazin-4-one;

6-[[(1,1-Dimethylethoxy)carbonyl]amino]-5-methyl-2-[isopropyl(methyl)amino]-4H-3,1-benzoxazin-4-one;

6-[[(1,1-Dimethylethoxy)carbonyl]amino]-5-methyl-2-[(4-furoyl)piperazinyl]-4H-3,1-benzoxazin-4-one;

6-[[(1,1-Dimethylethoxy)carbonyl)amino]-5-methyl-2-[[(2-cyano)ethyl]-(cyclopropyl)amino]-4H-3,1-benzoxazin-4-one;

6-[[(1,1-Dimethylethoxy)carbonyl]amino]-5-methyl-2-[(4-thenoyl)piperazinyl]-4H-3,1-benzoxazin-4-one;

6-[[(1,1-Dimethylethoxy)carbonyl]amino]-5-methyl-2-[(4-benzenesulfonyl)-piperazinyl]-4H-3,1-benzoxazin-4-one;

6-(benzoylamino)-5-methyl-2-[methyl(phenylmethyl)amino]-4H-3,1-benzoxazin-4-one;

6-[(phenylmethoxyacetyl)amino]-5-methyl-2-(diisopropylamino)-4H-3,1-benzoxazin-4-one;

6-[(2,4,6-Trifluorobenzoyl)amino]-5-methyl-2-(diisopropylamino)-4H-3,1-benzoxazin-4-one;

6-[[(1,1-Dimethylethoxy)carbonyl]amino]-5-methyl-2-[[methyl(4-dimethylamino)-phenylmethyl]-amino]-4H-3,1-benzoxazin-4-one;

6-[[(1,1-Dimethylethoxy)carbonyl]amino]-5-methyl-2-[methyl(2-pyridylmethyl)-amino]-4H-3,1-benzoxazin-4-one;

6-[[(1,1-Dimethylethoxy)carbonyl]amino]-5-methyl-2-[methyl[2-(3-indolyl)ethyl]amino]4H-3,1-benzoxazin-4-one;

6-[[(1,1-Dimethylethoxy)carbonyl]amino]-5-methyl-2-(4-morpholyl)-4H-3,1-benzoxazin-4-one;

6-[[(1,1-Dimethylethoxy)carbonyl]amino]-5-methyl-2-[allyl(methyl)amino]-4H-3,1-benzoxazin-4-one;

6-[[(1,-Dimethylethoxy)carbonyl]amino]-5-methyl-2-(1-decahydroquinolyl)-4H-3,1-benzoxazin-4-one; and 6-[[(1,1-Dimethylethoxy)carbonyl]amino]-5-methyl-2-[4-(1-acetylpiperadinyl)]-4H-3,1-benzoxazin-4-one.

* * * * *